United States Patent [19]

Nelson et al.

[11] Patent Number: 5,241,469
[45] Date of Patent: Aug. 31, 1993

[54] METHOD AND APPARATUS FOR AUTOMATED SPIROMETRY DATA ACQUISITION AND PROCESSING

[75] Inventors: Rodger C. Nelson, Issaquah, Wash.; F. Brian Ginn, Houston, Tex.

[73] Assignee: Micro Development Technologies, Inc., Houston, Tex.

[21] Appl. No.: 558,691

[22] Filed: Jul. 25, 1990

Related U.S. Application Data

[63] Continuation-in-part of Ser. No. 535,777, Jun. 11, 1990, abandoned.

[51] Int. Cl.[5] .......................... G06F 15/00; A61B 5/02
[52] U.S. Cl. .................... 364/413.03; 128/716; 128/717; 395/275
[58] Field of Search ................ 364/413.03; 128/716, 128/717, 729; 73/198; 395/275

[56] References Cited

U.S. PATENT DOCUMENTS

| | | | |
|---|---|---|---|
| D. 260,885 | 9/1981 | Jones | D14/106 |
| 3,726,270 | 4/1973 | Griffis et al. | 128/719 |
| 3,726,271 | 4/1973 | Mondshine et al. | 128/720 |
| 4,047,521 | 9/1977 | Kramer et al. | 128/725 |
| 4,078,554 | 3/1978 | Le Maitre | 128/726 |
| 4,418,701 | 12/1983 | Luijpers | 128/729 |

*Primary Examiner*—Roy N. Envall, Jr.
*Assistant Examiner*—Frantzy Poinvil
*Attorney, Agent, or Firm*—Vaden, Eickenroht, Thompson, Boulware & Feather

[57] ABSTRACT

A method and apparatus which include a special purpose cable and printed circuit board adapted for use with and installation in a personal computer for the specific purpose of automated acquisition and processing of analog spirometry and temperature data. The cable has on one end an interchangeable connector that is plugged into a volumetric spirometer. A temperature sensor is placed within the body of the connector and external to the sheaths of the cable and transmits analog data to the board via lines within the sheaths of the cable. The board provides an excitation voltage signal via the cable to the volumetric spirometer and receives analog data from the spirometer. The board then filters the analog spirometry and temperature data and alternately switches the data to an A/D converter by virtue of a signal selector. The A/D converter is enabled by the output of a comparing address and clocked by a frequency divided signal provided by a timing device. The A/D converter converts the filtered, switched analog data to digital form with 12-bit resolution and outputs it to the computer's data bus. The board furthermore has an onboard power regulator for providing 5-volt analog and digital operating power and reference signals.

5 Claims, 6 Drawing Sheets

METHOD AND APPARATUS FOR AUTOMATED SPIROMETRY DATA ACQUISITION AND PROCESSING

BACKGROUND OF THE INVENTION

This application is a continuation-in-part application of U.S. patent application Ser. No. 07/535,777 now abandonned filed Jun. 11, 1990 entitled "METHOD AND APPARATUS FOR AUTOMATED SPIROMETRY DATA ACQUISITION AND PROCESSING".

1. Field of the Invention

This invention pertains to automated acquisition and processing of spirometry data. More particularly, this invention pertains to automated acquisition and processing of data from a volumetric spirometer and an accompanying temperature sensor with a special purpose printed circuit board adapted for installation in a personal computer and a special purpose cable.

2. Description of the Prior Art

The use of spirometers in measuring pulmonary functions is well known in the art. These devices typically measure lung volume for health purposes. Although spirometry has been performed for many years in a hospital environment, the use of spirometers in the work place is relatively new. The use of these instruments in the work place originated in the textile industry to detect diseases resulting from cotton dust exposure. Since that time the use of spirometers has spread greatly into other industries. Workers in these industries are given periodic pulmonary function tests with spirometers to assist in monitoring the effect of work place exposure on the lungs.

There are two basic types of spirometers. The first is a pneumotach or flow spirometer which measures lung volumes indirectly during inhalation and exhalation and calculates lung volume from the data. The second type is a volumetric spirometer. The displacement of the spirometer element is directly proportional to lung capacity and therefore yields a direct measure of lung capacity. The current invention is specifically adapted for use with volumetric spirometers.

SensorMedics has produced a system which uses a multi-purpose 12-bit analog to digital (A/D) printed circuit board produced by Metrabyte, Inc. for spirometer data analysis. Because the Metrabyte board is multi-purpose, it requires unnecessary integrated circuits and analog communications channels, which increases electronics and inflates the price of the board.

It is therefore an object of this invention to provide an improved printed circuit board for installation in personal computers that is especially adapted to receive analog data from a volumetric spirometer and convert it to digital form with 12-bit resolution. The present invention meets the standards of the American Thoracic Society in a manner that is simpler, more efficient, and more cost effective to mass produce than any prior manner.

It is a further object of this invention to provide an improved printed circuit board and cable for installation in a personal computer that is optimally designed for the specific purpose of acquisition and processing data from a volumetric spirometer that will require no adaptations or components external to the special purpose board and cable.

It is still a further object of this invention to provide an improved printed circuit board for installation in a personal computer that can output 12-bits of digital data to an 8-bit data bus without having additional circuitry to multiplex the digital data.

It is a still further object of this invention to provide an improved cable that can be adapted for use with many different types of potentiometers and contains a temperature sensor through which data from the volumetric spirometer and from the temperature sensor may be transmitted through to a personal computer.

SUMMARY OF THE INVENTION

The invention comprises a specially designed cable and a printed circuit board for acquisition and processing of analog data from a volumetric spirometer and temperature sensor. The cable has a connector on one end that plugs into the volumetric spirometer. This connector is interchangeable in order to match various types of connectors used with various volumetric spirometers. The cable incorporates a temperature sensor at or near the spirometer end of the cable, housed within the interchangeable connector. The cable transmits analog data from both the spirometer and the temperature sensor to the board. The board itself is designed to plug into a personal computer. The board interfaces with the computer bus via a bus connector. The board also interfaces with the cable via a cable connector. The board is adapted to convert the analog data from the volumetric spirometer and temperature sensor to digital data for processing by the computer through an A/D converting means. The board has onboard voltage regulation means that receives power from the computer bus via the bus connector. The voltage regulation means provides regulated power to other onboard components, supplies reference signals to other onboard components, and supplies excitation signals to the spirometer and temperature sensor. The board further includes a temperature data filtering means for filtering electronic noise from the signals received via the cable connector.

The timing means divides the frequency of the computer's system clock to provide a clock signal for the A/D converting means. The address comparing means receives address data from the computer, analyzes and enables the board when directed to by the computer. The signal selection means receives additional addressing data and analyzes it in conjunction with the enabling signal from the address selection means to determine whether spirometry or temperature data is enabled to the A/D converting means. The 12 bits of digital data from the A/D converting means are transmitted to the computer in two 8-bit bytes.

BRIEF DESCRIPTION OF THE DRAWINGS

So that the manner in which the above recited features, advantages and objects of the invention, as well as others that will become apparent, are attained and can be understood in detail, a more particular description of the invention briefly summarized above may be had by reference to the exemplary preferred embodiment thereof illustrated in the drawings, which form a part of this specification. It is to be noted, however, that the appended drawings illustrate only the typical preferred embodiments and are not to be considered limiting of the scope as the invention may admit to other equally effective embodiments.

In the drawings.

DETAILED DESCRIPTION OF THE PREFERRED EMBODIMENTS

Figure 1:
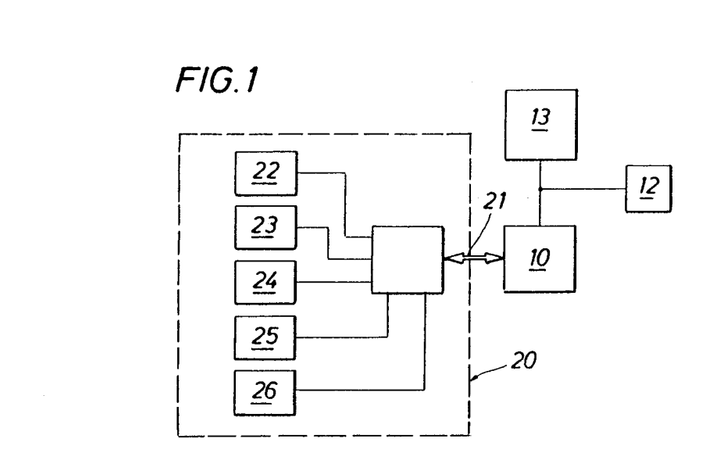
FIG. 1 illustrates the relationship of the invention to various elements of a personal computer, peripheral devices, and a volumetric spirometer.

Referring to FIG. 1, the present invention comprises a 12-bit A/D board 10 and special purpose cable 11. Cable 11 has a temperature sensor 12. Cable 11 receives analog data from volumetric spirometer 13 as well as the temperature sensor 12. Board 10 is adapted to be installed inside computer 20. In the contemplation of the preferred embodiment, computer 20 is an "IBM Model PC", "XT", or "AT", (IBM and each model designation being registered trademarks of International Business Machines) or a personal computer compatible to any of those models. Computer 20 comprises a bus 21, a monitor 22, keyboard 23, printer 24, floppy disk drive 25, and hard drive 26. As used herein, bus 21 is composed of the address, control, and data buses, a single bus in one of the aforementioned IBM models. Computer 20 operates in response to software stored on a floppy disk in disk drive 25 or on hard drive 26 and enables board 10 via bus 21 to begin automated acquisition and processing of analog spirometry and temperature data. Typically, computer 20 displays processed data on monitor 22, prints the data on printer 24 and stores the data on hard disk 26. Other types of peripheral devices, such as a modem, mouse, or plotter may be part of computer 20.

Figure 2:
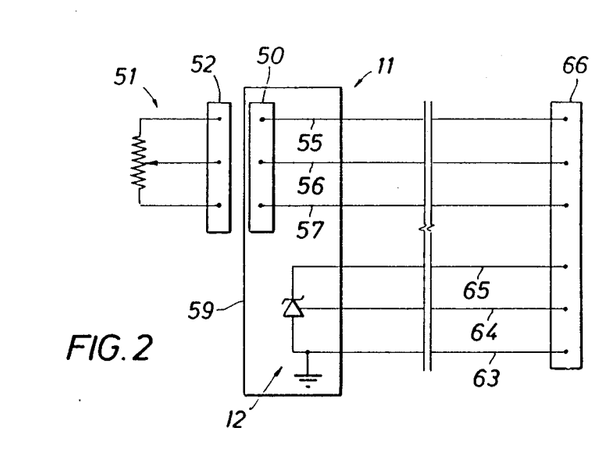
FIG. 2 is a illustration of the special purpose cable of the invention.

A preferred embodiment of the present invention comprises, in part, cable which is illustrated in greater detail in FIG. 2. One end of cable 11 has connector 50 that is interchangeable so that it can be adapted to plug into the potentiometer 51 of volumetric spirometer 13. Not all commercially available volumetric spirometers are equipped with a potentiometer to translate the mechanical displacement of the spirometer element into electrical signals. Volumetric spirometers lacking potentiometers must consequently be equipped with one before the invention can be practiced. Even where spirometers are equipped with potentiometers, different spirometers often do not employ the same connector 52, hence the need for the interchangeable nature of connector 50. The connector 50 has a pin tied to each of lines 55–57. Line 55 transmits an excitation signal from board 10 via cable connector 109 (not shown in FIG. 2) to potentiometer 51. Line 57 provides signal ground while line 56 transmits the resulting electrical signal from potentiometer 51 indicative of the displacement of the spirometer element and the potentiometer 51 to board 10. Temperature sensor 12 is an integrated circuit contained within the body 59 of connector 50 but outside the sheath of cable 11. Sensor 12 in the presently preferred embodiment is a National Semiconductor Corporation precision intergated circuit temperature sensor identified as LM335. Line 63 provides temperature ground while line 64 provides adjustment that permits calibration of sensor 12. Temperature data is transmitted via line 65 to board 10. Cable is further comprised of second connector 66 selected to match cable connector on board 10.

Figure 3:
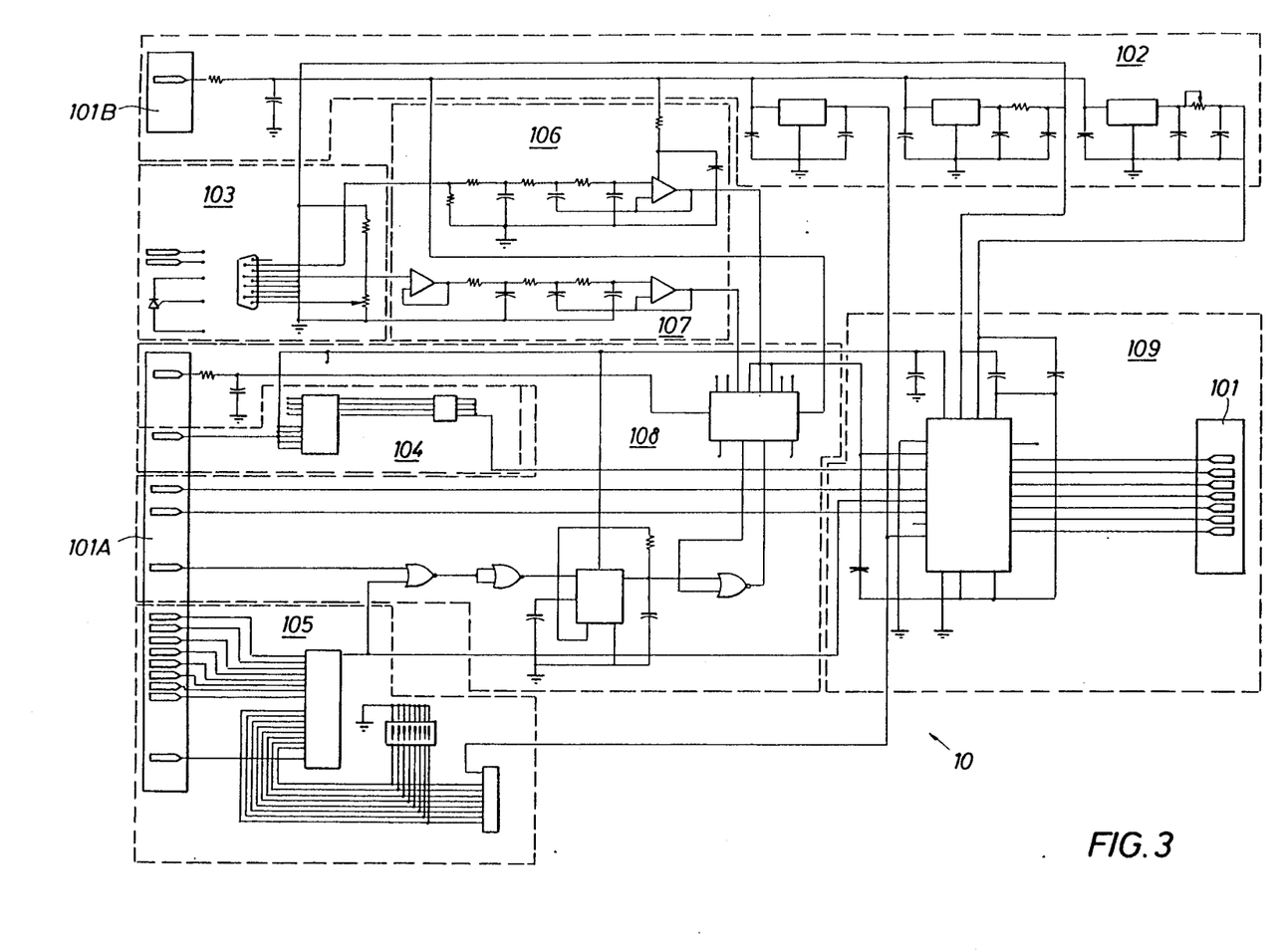
FIG. 3 is a block diagram of the printed circuit board's circuitry.

Board 10 is illustrated in the block diagram of the board circuitry in FIG. 3. Board 10 includes an A/D converting means 109. Board bus connector 101, shown as 101A, 101B and 101C, connects the board 10 to the computer bus 21 of computer 20. Voltage regulation means 102 provides both analog and digital power to the board 10. Voltage regulation means 102 furthermore supplies an analog voltage reference signal to A/D converting means 109, as well as an excitation voltage signal to temperature sensor 12 and spirometer 13 via cable connection means 103 and line 55 of cable 11. A/D converting means 109 receives its clock signal from timing means 104. Addressing means 105 determines when the board 10 is to be enabled. Timing means 104 and address comparing means 105 each receive timing, address and control signals via computer bus 21 and board bus connector 101. Analog data from temperature sensor 12 and spirometer 13 transmited via cable 11 is received by cable connector means 103 of board 10 and filtered by filtering means 107 and 106. The filtered data from filtering means 106 and 107 is received by signal selection means 108. A/D converting means 109 receives the filtered data either from temperature filtering means 107 or spirometry filtering means 106 as switched by signal selection means 108 When enabled by the output of address comparing means 105.

Figure 4:
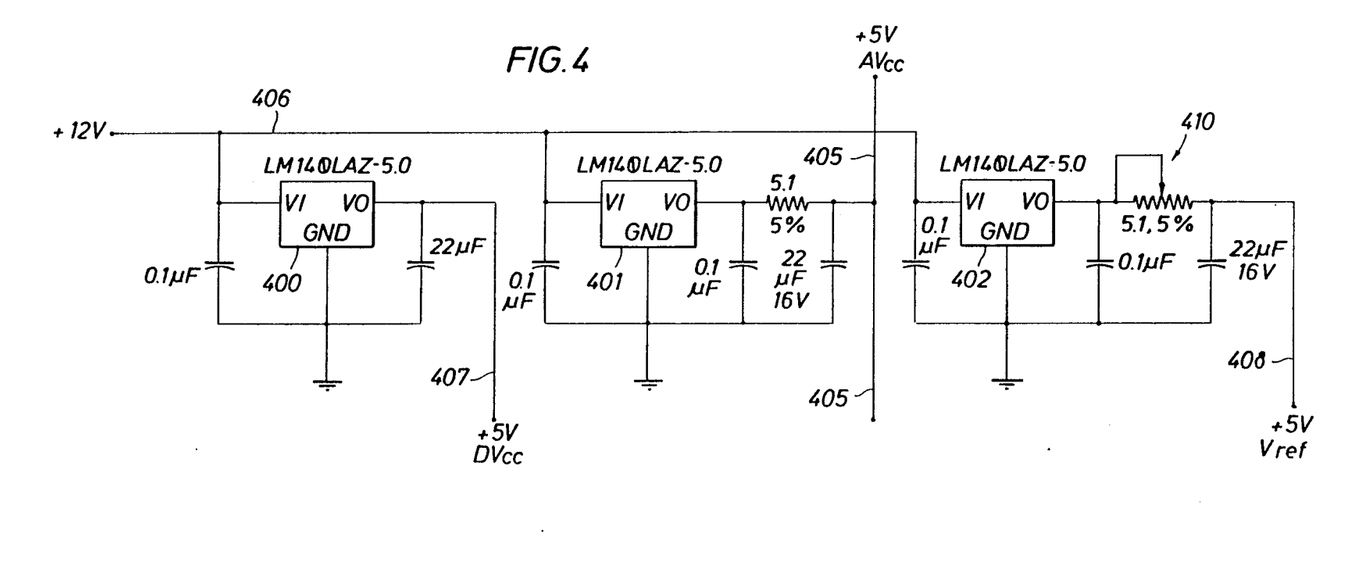
FIG. 4 is a detailed drawing of the power regulating and supply means.

Voltage regulation means 102 is illustrated in further detail in FIG. 4. Voltage regulators 400–402 in the presently preferred embodiment are each LM140LAZ-5.0 voltage regulators. Regulator 400 provides digital $V_{cc}$, regulator 401 provides analog $V_{cc}$, and regulator 402 provides analog $V_{ref}$ for board 10. Each of regulators 400–402 receives +12 volts from bus 21 via bus connector 101 and line 406 and regulates it to +5 volts. It is important that analog $V_{cc}$ on line 405 and analog $V_{ref}$ on line 408 are matched to insure proper operation of A/D converting means 109. While the presently preferred embodiment accomplishes this by using variable resistor 410, it is contemplated that regulator 402 may be replaced with an adjustable voltage regulator as is well known to those of ordinary skill in the art.

Figure 5:
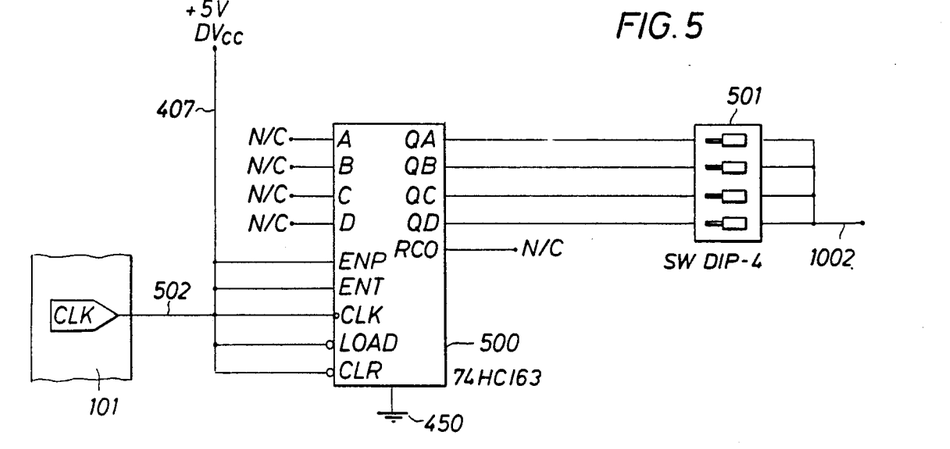
FIG. 5 is a detailed drawing of the timing means.

Timing means 104 is illustrated in FIG. 5. Timing means 104 is comprised of counter 500 and dip switch 501. In the presently preferred embodiment, counter 500 is a 74HC163. Counter 500 receives the clock signal from computer 20 via bus 21 and bus connector 101 on the clock line 502. Counter 500 increments its count each time it receives a pulse on clock line 502 and generates an output signal on line 1002. When the incremental amount equals the value stored in the individual switch settings of dip switch 501. Timing means 104 thereby effectively divides the system clock of computer 20 by the dividend stored in dip switch 501 in order to obtain a timing signal for A/D converting means 109. This allows board 10 to be used in a variety of computers having different operating frequencies.

Figure 6:
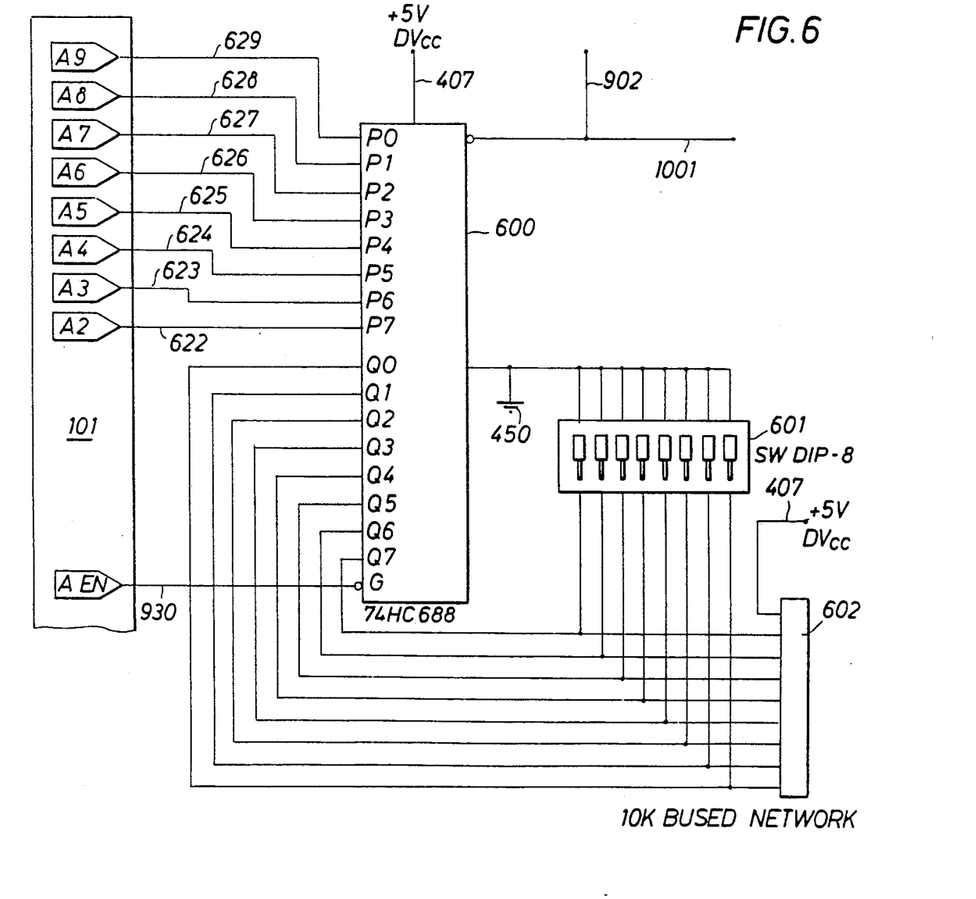
FIG. 6 is a detailed illustration of the address comparing means.

FIG. 6 illustrates address comparing means 105 in greater detail. Comparator 600 receives addressing data on lines 622-629 from bus 21 via bus connector 101. Comparator 600 is enabled by a signal on line 930 that is also received via bus 21 and bus connector 101. The settings of dip switch 601 determine the address of board 10 in computer 20. When comparator 600 is enabled, it compares the data on lines 622-629 with the settings of dip switch 601 to determine whether CPU 13 is addressing the board and, if so, outputs a signal on line 902 and on line 1001. Comparator 600 does not otherwise output a signal. Bused network 602 provides a current buffer for individual switches of dip switch 601 when the switches are set to logic zero.

Figure 7:
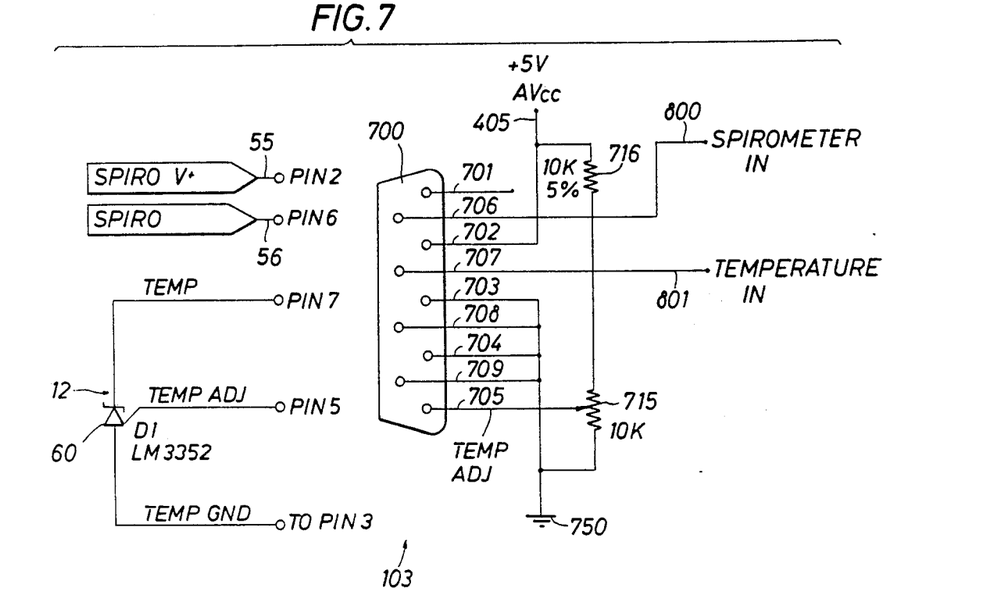
FIG. 7 is a detailed drawing of the cable connector and its pin assignments.

Cable connection means 103 is illustrated in greater detail in FIG. 7. Connection means 103 includes a connector 700 which is on board 10. Connector 700 in the presently preferred embodiment is an Amp 745781-4. Lines 703-05 and 708-09 are tied to analog system ground 750. Line 706 receives spirometry data from spirometer 13 via line 55 of cable 11 and transmits the analog spirometry data to filtering means 106 via line 800. Line 702 of connector 700 receives a +5 voltage analog $V_{cc}$ signal, which is a voltage excitation signal for spirometer 13 via line 405 from voltage regulating means 104, and transmits it to spirometer 13 via line 55 of cable 11. Analog temperature data is received from temperature sensor 12 via line 65 of cable 11 through line 707 of connector 700. The calibration signal for temperature sensor 12 is transmitted through line 705 of connector 700 via line 64 of cable 11. Calibration of temperature data received through line 707 of connector 700 is accomplished by adjusting the setting of 10 KΩ variable resistor 715 operating in conjunction with 1 KΩ resistor 716. The calibrated temperature data is transmitted to temperature filtering means 107 via line 801. Board 10 may therefore be calibrated for operation specifically with a cable 11 and requires recalibration in the event board 10 is used with another cable.

Figure 8:
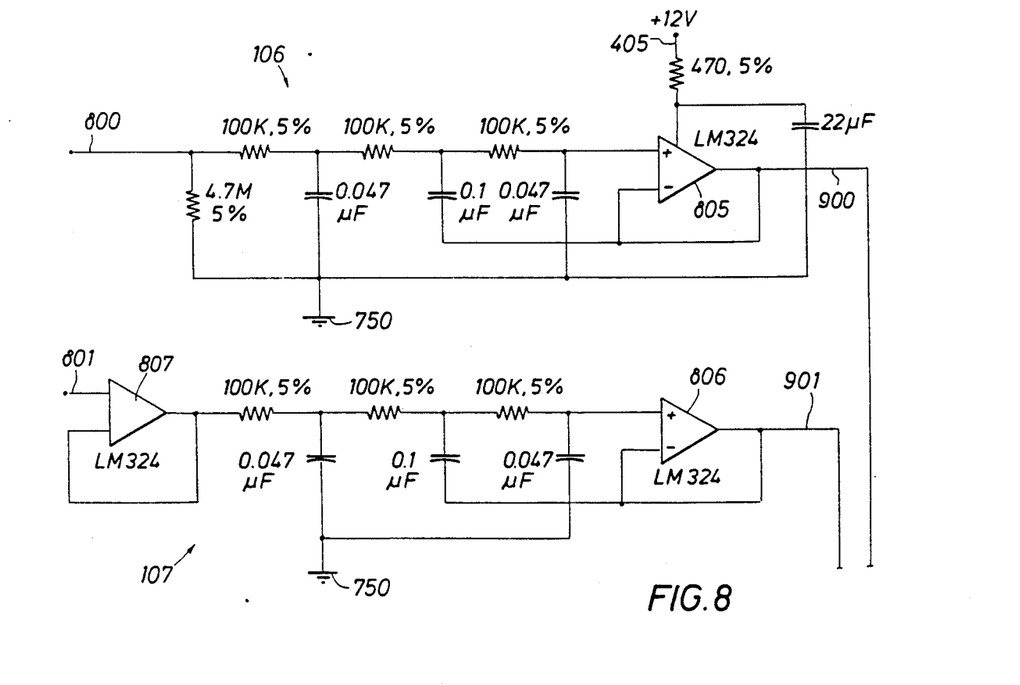
FIG. 8 is a detailed drawing of the temperature and spirometry data filtering means.

Filtering means 106 and 107 are further illustrated greater detail in FIG. 8. Filtering means 106 filters the spirometry data received via line 800 and is comprised of an RC network and amplifier 805 that outputs the filtered, analog data on line 900. Temperature data filtering means 107 receives analog temperature data via line 801 and is comprised of an RC network in combination with amplifiers 806 and 807. The filtered, analog temperature data is output on line 901. Amplifiers 805 through 807 in the presently preferred embodiment are contained in an LM324 quad operational amplifier.

Figure 9:
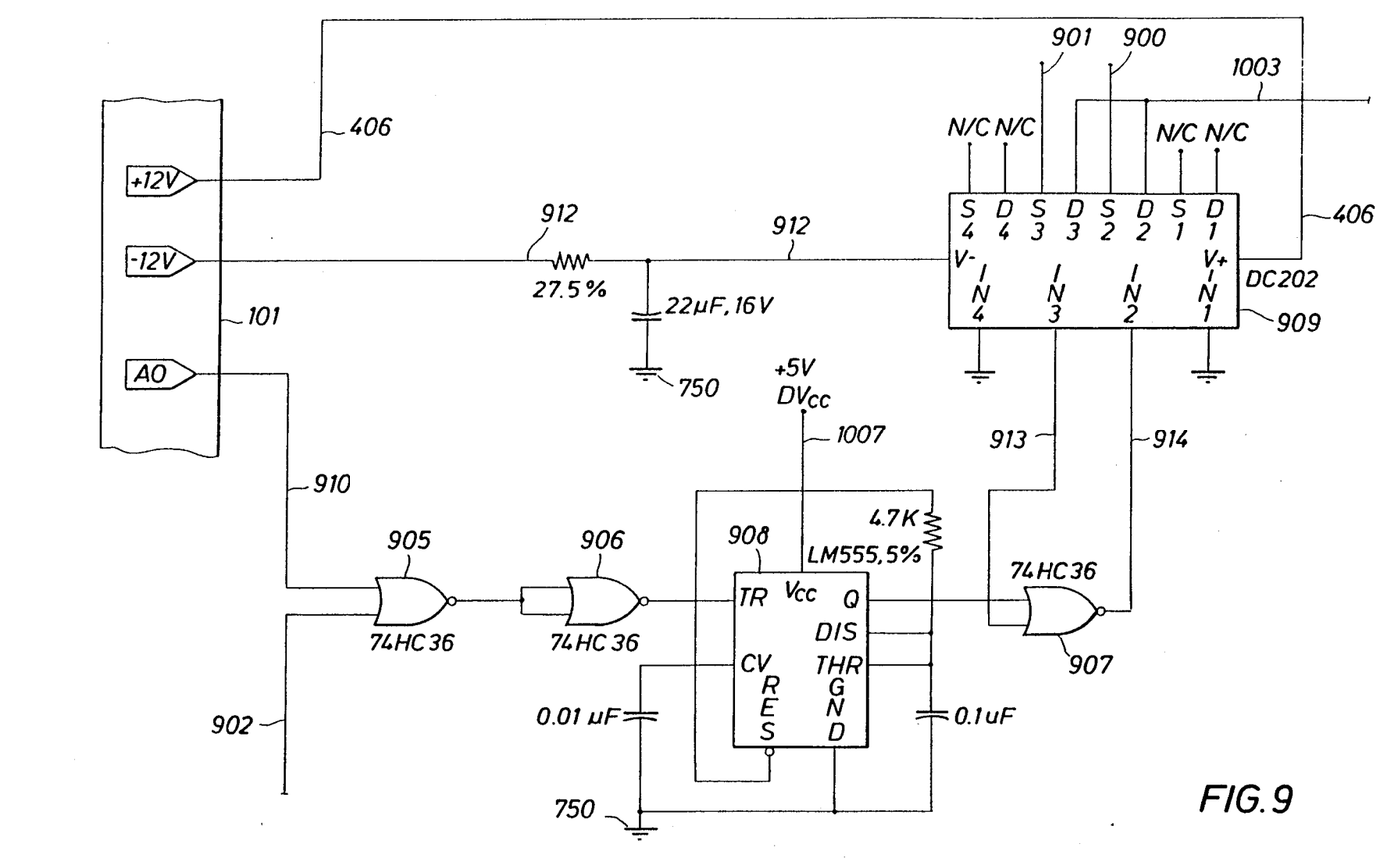
FIG. 9 is a detailed drawing of the signal selection means.

Referring now to FIG. 9, signal selection means 108 is comprised of NOR gates 905-907, timer chip 908, and analog multiplex switch 909. In this embodiment, NOR gates 905-907 are contained in a 74HC36 quad positive NOR gate chip, timer chip 908 is an ICM7555 timer, and analog multiplexed switch 909 is a DG202 quad monolithic SPST CMOS analog switch.

Figure 9A:
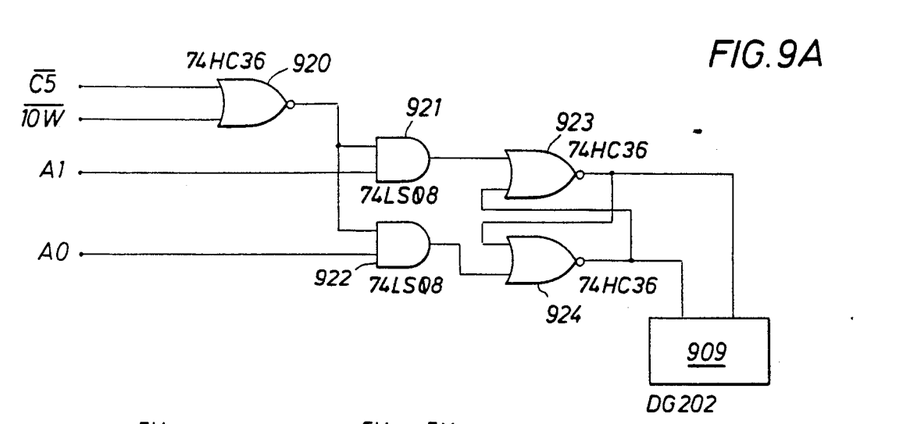
FIG. 9A depicts an alternative embodiment of the signal selection means shown in FIG. 9.

Alternately, referring to FIG. 9A, signal selection means 108 is comprised of NOR gate 920, AND gates 921-922, NOR gates 923-924, and analog switch 909. NOR gates 920, 923-924 are contained in a 74HC36 quad positive NOR gate chip. AND gates 921-922 are contained in a 74LS08 quad 2-input positive AND gate chip. Analog switch 909 is a DG202 quad monolithic SPST CMOS analog switch.

Signal selection means 108 as described in FIG. 9 uses address signal A0, from bus 21, as a control signal to determine whether spirometry or temperature data should be selected. This configuration allows data from either source to be selected at the time every request for data is made. On the otherhand, signal selection means 108 as described in FIG. 9A uses IOW (active low), from bus 21, in conjunction with the output of address comparing means 105 to enable the data latch which uses A0 and A1, from bus 21, to select either spirometry data or temperature data. Software sends control signals via A0 and A1 to switch between spirometry data and temperature data. Requests for data no longer require selection information.

Signal selection means 108 receives input from address comparing means 105 via line 902 and an address signal from bus 21 via bus connector 101 on line 910 as well as a negative 12-volt input from bus 20 via connector 101 on line 912. Switch 909 receives filtered analog data from filtering means 106 and 107 via lines 900 and 901, respectively. Switch 909 then switches either spirometry or temperature data onto line 1003 in accord with control signals received on lines 913 and 914. Signal selection means 108 thereby selects either spirometry data or temperature data as input to A/D converting means 109 in accord with control signals received from the computer 20 via bus 21. It is signal selection means 108 that enables the invention to optimally receive input from only two channels, i.e., select spirometry or temperature data, while outputting both types of data onto a single 8-bit bus with 12-bit resolution via A/D converting means 109.

Figure 10:
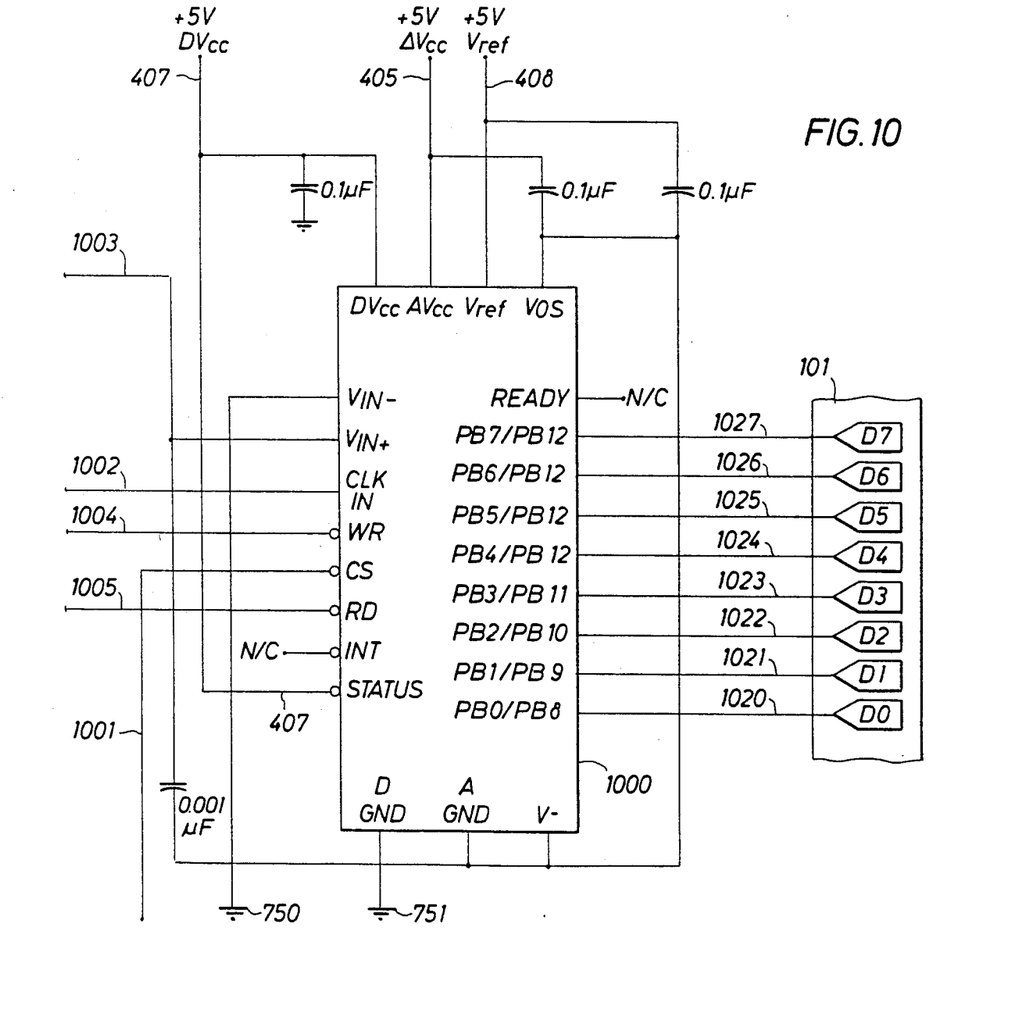
FIG. 10 is a detailed drawing of the A/D converting means.

A/D converting means 109 is illustrated in FIG. 10. The converting means 109 includes a 12-bit A/D converter 1000 which receives analog data and transmits 12 bits of digital data to the computer 20 in two 8-bit bytes. A/D converter 1000 in the primarily preferred embodiment is a National Semiconductor ADC1205 12-bit plus sign A/D converter. Converter 1000 is clocked by a timing signal received on line 1002 and is further controlled by read and write command signals received on lines 1004 and 1005 via bus 21 and bus connector 101. Converter 1000 is enabled by a signal received via line 1001 from address comparing means 105. Converter 1000 is furthermore tied to digital $V_{cc}$ ($DV_{cc}$) via line 407, analog $V_{cc}$ ($AV_{cc}$) via line 405, and analog voltage reference $V_{ref}$ via line 408 as well as to digital system ground 751 and analog system ground 750. A/D converter 1000 receives analog data from signal selection means 108 via line 1003, converts it to 12-bit digital form, and outputs it in digital form, 8-bits at a time, to bus 21 on lines 1020-1027 via bus connector 101. It will be understood that certain features and subcombinations are of utility and may be employed without reference to any of the features and subcombination. This is contemplated by and is within the scope of the claims. Because many possible embodiments may be made of the invention without departing from the scope thereof, it is to be understood that all matter herein set forth or shown in the accompanying drawings is to be interpreted as illustrative and not in a limiting sense.

What is claimed is:

1. A printed circuit board for use in data acquisition and processing of analog data from a volumetric spirometer and a temperature sensor for installation in a personal computer having a computer bus and a central processing unit, comprising:

a first connector through which spirometry analog data from the volumetric spirometer and temperature analog data from the temperature sensor is received;

a second connector through which an addressing signal is received from the computer bus;

address selection means for processing the address signal received from the computer bus through said second connector and outputting an enabling signal when an instruction for the printed circuit board is received from the central processing unit;

means for filtering the spirometry analog data received through said first connector;

means for filtering the temperature analog data received through said first connector;

switching means for multiplexing the filtered spirometry analog data and the filtered temperature analog data when the enabling signal is received from said address selection means; and means for converting the analog data multiplexed by said switching means to digital form with 12-bit resolution and transmitting the converted data in 8-bit bytes to the computer bus, said converting means operating only when the enabling signal is received from said address selection means.

2. The printed circuit board of claim 1 wherein said switching means is a two channel analog switch.

3. A printed circuit board for use in data acquisition and processing of analog data from a volumetric spirometer and a temperature sensor for installation in a personal computer, comprising:

a first connector that receives analog data from a volumetric spirometer and from a temperature sensor;

a first noise filter that filters the analog data received from the volumetric spirometer via said first connector;

a second noise filter that filters the analog data received from the temperature sensor via said first connector;

a second connector that receives a timing signal, a voltage supply signal, and address data from the central processing unit of the computer and transmits data to the computer;

an address selector that determines from the address data received by said second connector whether the board has been addressed by the central processing unit of the computer and for outputting an enabling signal when the board is addressed;

a frequency divider that divides the frequency of the timing signal received by said second connector and outputs a clock signal;

a data selector that determines from the address data received by said second connector and from the enabling signal output from said second connector and from the enabling signal output from said address selector whether the central processing unit of the computer is seeking spirometry data or temperature data and outputs a switch control signal;

an analog switch that outputs either the analog data filtered by said first filter or the analog data filtered by said second filter in response to the switch control signal;

an analog-to-digital converter that receives the clock signal output by said frequency divider and that receives the switched analog data from said analog switch, converts the analog data to digital form with 12-bit resolution when said converter receives the enabling signal, and outputs the digital data in 8-bit bytes;

a first voltage regulator that regulates the voltage supply signal received by said second connector and outputs digital power to said address selector, said frequency divider, said data selector, and said analog-to-digital converter;

a second voltage regulator that regulates the voltage supply signal received by said second connector and outputs analog power to said data selector, said first noise filter, said second noise filter, said analog multiplex switch, and said analog-to-digital converter;

a third voltage regulator that regulates the voltage supply signal received by said second connector and outputs an analog reference voltage signal to said analog-to-digital converter.

4. A method of processing analog data from a volumetric spirometer and from a temperature sensor with a printed circuit board in a computer system, comprising the steps of:

enabling the printed circuit board;

receiving the analog data from the volumetric spirometer;

receiving the analog data from the temperature sensor;

filtering the received spirometry analog data and the received temperature analog data;

switching for selecting between the filtered spirometry data and the filtered temperature data;

converting the selected data to digital form with 12-bit resolution; and transmitting the converted data in two 8-bit bytes to the computer.

5. The method of claim 4 further comprising the step of multiplexing the converted data during said step of outputting the converted data to the computer.

* * * * *